United States Patent [19]

Saito et al.

[11] Patent Number: 4,973,720
[45] Date of Patent: Nov. 27, 1990

[54] PROCESS FOR THE PREPARATION OF P-BENZOQUINONE

[75] Inventors: Toranosuke Saito, Osaka; Kenichi Ikemoto, Kumamoto; Hiroki Tsunomachi, Osaka; Katsuya Sakaguchi, Fukuoka, all of Japan

[73] Assignee: Sanko Kaihatsu Kagaku Kenkyusho, Ibaraki, Japan

[21] Appl. No.: 253,056

[22] Filed: Oct. 4, 1988

[30] Foreign Application Priority Data

Oct. 16, 1987 [JP] Japan ................ 62-259747

[51] Int. Cl.$^5$ .................. C07C 46/06; C07C 50/04
[52] U.S. Cl. ................................................ 552/293
[58] Field of Search ................ 260/396 R; 552/293

[56] References Cited

U.S. PATENT DOCUMENTS 3,834,997  9/1974  Hocking et al. ............... 260/396 R
4,482,493  11/1984  Matsumoto ..................... 260/396 R

FOREIGN PATENT DOCUMENTS 1338462  9/1963  France .

OTHER PUBLICATIONS

*Organic Syntheses*, col. vol. II, p. 553 (1943), "Quinone", H. W. Underwood and W. L. Walsh.
*Organic Syntheses*, col. vol. I, pp. 482–484 (1956), "Quinone", E. B. Vliet.

*Primary Examiner*—Vivian Garner
*Attorney, Agent, or Firm*—Jeffers, Hoffman & Niewyk

[57] ABSTRACT

There is provided a process of producing p-benzoquinone, wherein hydroquinone and hydrogen peroxide are reacted in water, an aqueous inorganic acid solution, an inert organic polar solvent or a mixture of water with an inert organic polar solvent in the presence of a catalyst selected from the group consisting of iodine, hydrogen iodide, and iodine compounds of metals.

According to the process, p-benzoquinone can be obtained from hydroquinone with the yield and the quality of the p-benzoquinone being high without requiring any special facilities, equipments and operations.

5 Claims, No Drawings

PROCESS FOR THE PREPARATION OF P-BENZOQUINONE

BACKGROUND OF THE INVENTION

The present invention relates to a process for the preparation of p-benzoquinone by reacting hydroquinone with hydrogen peroxide. P-benzoquinone is a quite useful compound as an intermediate, for example, for polymerization inhibitors, unsaturated polyester stabilizers, aromatic polyester monomer raw materials, medicines, agricultural chemicals, and dyes.

Prior Art

Conventionally, various methods are known of producing p-benzoquinone by oxidizing hydroquinone, and typical ones are:

(1) a process wherein hydroquinone is oxidized with sodium chlorate at 40° C. using a 2% aqueous sulfuric acid as a medium and vanadium pentoxide as a catalyst [Organic Syntheses, Col. Vol. II, 553 (1943)], (2) a process wherein hydroquinone is oxidized with oxygen in an acetic acid medium using 5% ruthenium-carbon as a catalyst (French Patent No. 1,338,462), and (3) a process wherein hydroquinone is oxidized with sodium dichromate using water acidified with sulfuric acid as a medium [Organic Syntheses, Col. Vol. I, 482 (1956)].

However, these processes require further improvements from an industrial point of view because the catalysts and the oxidizing agents used are expensive, the processes are accompanied by safety and hygienic problems and waste water treatment problems, and the yield and the quality of the intended product are required to be further improved.

SUMMARY OF THE INVENTION

The inventors have intensively studied industrially advantageous processes free from the above problems, and have reached the present invention.

According to the present invention, there is provided a process of producing p-benzoquinone, wherein hydroquinone and hydrogen peroxide are reacted in water, an aqueous inorganic acid solution, an inert polar organic solvent or a mixture of water with an inert polar organic solvent in the presence of a catalyst selected from the group consisting of iodine, hydrogen iodide, and iodine compounds of metals.

According to the present process, high quality p-benzoquinone can be obtained from hydroquinone in a high yield without requiring any special facilities, equipments and operations, and any particular measures against safety and hygiene problems and public hazard, which means the present process can be carried out industrially quite advantageously.

DETAILED DESCRIPTION OF THE INVENTION

The present invention provides a process of producing p-benzoquinone by using iodine, hydrogen iodide, or an iodine compound of a metal as a catalyst when hydroquinone is oxidized with hydrogen peroxide in a liquid phase.

As the catalyst, use is made of simple iodine, hydrogen iodide or a iodine compound of a metal. As the iodine compounds of metals are preferably used ones soluble in water before and after the reaction such as sodium iodide, potassium iodide, lithium iodide, zinc iodide, magnesium iodide, and iodates of alkali metals.

Generally, the amount of these catalysts to be used is 0.01 to 20% by weight (hereinafter the percentages quoted represent percent by weight), preferably 0.5 to 5% based on the hydroquinone.

The concentration of the hydrogen peroxide solution used in the present invention is generally 20 to 70% by weight, and preferably 35% by weight, which concentration is industrially most easily available. The amount of hydrogen peroxide to be used is preferably 0.8 to 2.0 times the amount of the hydroquinone in terms of mol.

As the medium used in the reaction, use can be made of water, or an aqueous solution of an inorganic acid such as a 0.5 to 10% aqueous sulfuric acid or hydrochloric acid solution, or an inert polar organic solvent such as methyl alcohol, ethyl alcohol, isopropyl alcohol, and ethylene glycol, or a mixture of water with one of the above polar organic solvents, with isopropyl alcohol, or a mixture of water with isopropyl alcohol preferable.

Although the amount of the reaction medium to be used depends on the solubility of hydroquinone, it is generally preferable that the amount is 2 to 3 times the hydroquinone in terms of weight. It is not necessarily required that all of the hydroquinone is dissolved in the medium.

The reaction temperature is generally 10° to 80° C., preferably 25° to 50° C. According to a preferable mode of the present invention, hydroquinone and a reaction medium are charged at room temperatures, then after iodine, hydrogen iodide or a metal iodine compound is added at 25° C., a hydrogen peroxide solution is added dropwise, then the temperature is raised to 45° to 50° C., and the temperature is retained for several hours to complete the reaction.

Since the reaction product obtained after the completion of the reaction in the above mode is quite low in solubility in the reaction medium, when it is filtered near at room temperatures, yellow crystals of p-benzoquinone can be easily obtained.

The thus obtained p-benzoquinone is high in quality and purity.

Further, the polar organic solvent used in the reaction can be recovered by simple distillation, and even if the recovered solvent contains water, the solvent can be used again in the reaction as it is.

EXAMPLES

Examples of the present invention are described below.

Example 1

55 g of hydroquinone, 115 g of isopropyl alcohol as a reaction medium, and 1 g of iodine as a catalyst were charged into a 300 ml four-necked glass reaction vessel with a stirrer, a dropping funnel, and a thermometer. Then stirring was started, and after 58 g of a 35% hydrogen peroxide solution were added over about 3 hours while keeping the temperature at 30° to 35° C., the temperature was raised to about 45° C., which was kept for about 3 hours to complete the reaction.

After the completion of the reaction, the reaction mixture was cooled gradually to about 15° C., and the reaction product was filtered by suction. The reaction product was washed with a small amount of isopropyl alcohol, and dried under reduced pressure to yield 49.5 g of p-benzoquinone. The yield was 91.6% (based on the charged hydroquinone, hereinafter the same being applied), the melting point was 111° to 112° C., and the purity resulted from high-speed liquid chromatography (the same being applied hereinafter) was 99.0%.

The filtered mother liquor containing isopropyl alcohol that had been obtained by filtering the reaction product by suction was distilled under normal pressures or reduced pressure in a usual manner to recover aqueous isopropyl alcohol containing about 12% of water. The recovered isopropyl alcohol can be used again as a reaction medium in the next reaction.

Example 2

Example 1 was repeated, except that the water-containing isopropyl alcohol recovered by distillation in Example 1 was used as a reaction medium. That is, 115 g of the isopropyl alcohol containing 12% of water recovered by distillation, 55 g of hydroquinone, and 1 g of iodine were charged into a reaction vessel. The reaction was effected using 58 g of a 35% hydrogen peroxide solution, then after the completion of the reaction, cooling, drying, washing, and then drying were effected to yield 49 g of p-benzoquinone. The yield was 90.7%, the melting point was 111.0° to 112.0° C., and the purity was 98.8%.

Example 3

Example 1 was repeated, except that 55 g of hydroquinone, 100 g of distilled water, and 1 g of iodine were charged into a reaction vessel, and the reaction was effected by using 58 g of a 35% hydrogen peroxide solution. After the completion of the reaction, cooling, filtering, and drying were effected to yield 46.5 g of p-benzoquinone. The yield was 86.1%, the melting point was 111.0° to 112.0° C., and the purity was 98.0%.

Example 4

Example 3 was repeated, except that a 3% aqueous dilute sulfuric acid was used instead of 100g of distilled water, thereby obtaining 48.5 g of p-benzoquinone. The yield was 89.8 %, the melting point was 111.0° to 112.0° C., and the purity was 98.5%.

Example 5

Example 1 was repeated, except that 2 g of potassium iodide dissolved in 5 g of water were used instead of 1 g of iodine, thereby obtaining 47.3 g of p-benzoquinone. The yield was 87.5%, the melting point was 111.0° to 112.0° C., and the purity was 98.8%.

Example 6

Example 1 was repeated, except that 2.2 g of hydriodic acid (containing 47% of HI) was used instead of 1 g of iodine, thereby obtaining 47.8 g of p-benzoquinone. The yield was 88.4%, the melting point was 111.0° to 112.0° C., and the purity was 98.7%.

What is claimed is:

1. A process of producing p-benzoquinone, wherein hydroquinone and hydrogen peroxide are reacted in water, an aqueous inorganic acid solution, an inert organic polar solvent or a mixture of water with an inert organic polar solvent in the presence of a catalyst selected from the group consisting of iodine, hydrogen iodide, sodium iodide, potassium iodide, lithium iodide, zinc iodide, magnesium iodide, and iodates of alkali metals.

2. A process as claimed in claim 1, wherein said iodine catalyst is used in an amount of 0.01 to 20 wt. % based on the hydroquinone.

3. A process as claimed in claim 1, wherein said hydrogen peroxide is an aqueous hydrogen peroxide solution having a concentration of 20 to 70% by weight.

4. A process as claimed in claim 1, wherein the molar ratio of said hydrogen peroxide to hydroquinone is from 0.8 to 2.0.

5. A process as claimed in claim 1, wherein said inert organic polar solvent is a member selected from the group consisting of methyl alcohol, ethyl alcohol, isopropyl alcohol, and ethylene glycol.

* * * * *